United States Patent [19]

Lesieur et al.

[11] Patent Number: 4,778,792

[45] Date of Patent: Oct. 18, 1988

[54] USE OF 7-ACYL BENZOXAZINONES AND THEIR DERIVATIVES IN TREATING ATHEROMATOUS DISORDERS

[75] Inventors: Isabelle Lesieur, Gondecourt; Charles Lespagnol; Ziaddine Moussavi, both of Lambersart; Jean-Claude Fruchart, Ennetieres en Weppes; Jacques Sauzieres, Versailles; Nicole Monfilliette, Villeneuve d'Asc, all of France

[73] Assignee: Laboratories Negma, France

[21] Appl. No.: 921,561

[22] Filed: Oct. 20, 1986

[30] Foreign Application Priority Data

Oct. 21, 1985 [FR] France ................... 85 15595

[51] Int. Cl.⁴ ............................. A61K 31/535
[52] U.S. Cl. ................... 514/230.5; 544/101; 544/105
[58] Field of Search ............. 544/101, 105; 514/231, 514/234, 237, 239

[56] References Cited

U.S. PATENT DOCUMENTS 3,770,734 11/1973 Pesson et al. ............... 544/105
4,358,455 11/1982 Atkinson et al. ............. 546/300 X

FOREIGN PATENT DOCUMENTS 2509155 9/1976 Fed. Rep. of Germany .
1560628 3/1969 France .

OTHER PUBLICATIONS

Baker, The Journal of Organic Chemistry, vol. 48, No. 25, (1983), pp. 5140-5143.

Primary Examiner—Richard L. Raymond

[57] ABSTRACT

The invention relates to products characterized by the general formula:

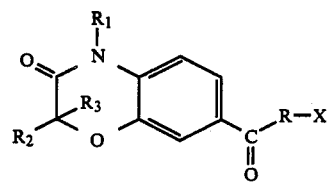

in which $R_1$, $R_2$, $R_3$, R and X have the meanings indicated in claim 1. The invention also related to pharmaceutical compositions administrable particularly orally, containing the abovesaid compounds in association with a pharmaceutically acceptable vehicle. They are useful as medicaments.

17 Claims, No Drawings

USE OF 7-ACYL BENZOXAZINONES AND THEIR DERIVATIVES IN TREATING ATHEROMATOUS DISORDERS

The invention relates to 7-acyl benzoxazinones (or 7-acyl (2H)-1,4-benzoxazine-3 (4H) ones) and derivatives of the latter, and a process for obtaining them.

The products of the invention are devoid of toxicity and show a wide range of pharmacological properties enabling their use in various therapeutic fields.

They have particularly important antiatherosclerosis properties as well as analgesic, anti-inflammatory, antimicrobial, anti-fungal and cardiovascular properties and effects on the central nervous system. The invention therefore relates also to pharmaceutical compositions containing these products in association with a pharmaceutically acceptable vehicle.

The products according to the invention are characterized by the general formula:

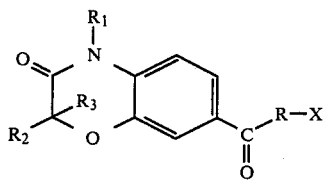

in which:
$R_1$ is either hydrogen group comprising from 1 to 6 carbon atoms, preferably alkyl, alkaryl or aralkyl, as the case may require, carrying substituents, particularly of the type envisaged below with respect to the group X, or a heterocyclic group, particularly thienyl, furyl, pyridinyl or pyridyl,
$R_2$ and $R_3$ are each, and this independently from one another, hydrogen or an alkyl group comprising from 1 to 6 carbon atoms,
R is a hydrogen group formed from cyclic or aliphatic elements, or both at once, comprising from 1 to 15 carbon atoms, or one of the above-said heterocyclic groups,
X is hydrogen or a carboxyl, halogen, hydroxyl, nitro, amino, itself substituted or not by one or two alkyl groups containing from 1 to 4 carbon atoms or a heterocyclic amino group, alkoxyl comprising from 1 to 4 carbon atoms, X being also capable of defining a chemical ring-forming bond formed between R and the carbon atom at the 6 position of the benzene ring of the benzoxazinone part of the molecule, as well as, if there is occasion, the corresponding salts or esters, and the optical isomers when $R_2$ and $R_3$ are different.

Preferably $R_1$, $R_2$, and $R_3$ are, independently of one another, hydrogens or methyl groups. In a first preferred class of compounds, denoted below for ease of language by the expression "compounds of group I", R is an aryl group particularly phenyl, arylalkyl or heterocyclic, alkaryl particularly benzyl, alkyl including here cyclopropyl, comprising from 1 to 6 carbon atoms or one of the above-said heterocyclic groups, X being a hydrogen or a halogen, particularly chlorine or bromine, a hydroxyl or an amino group, particularly piperazine, substituted or not, or again one of the above-said heterocyclic groups.

A second prefered class of compounds according to the invention is formed from alpha-beta ethylenic ketones in which the group R is an aliphatic chain of which the first carbon, at the alpha position of the carboxyl group is the carrier of an ethylenic branch group, particularly methylene. Preferably the group CO—R is then a 2-methylene butyryl group. These compounds will sometimes be denoted below by the expression "compounds of group II".

In a third class of preferred compounds according to the invention—formed by "Chalcones" or "compounds of group III", the group R is a —C=—X—X group, in which W is an alkyl, arylalkyl or aryl group, particularly —C=C—C$_6$H$_5$—X, X being hydrogen or a halogen, an amino group or hydroxyl, methoxyl or nitro.

In a fourth class of compounds, of the benzoxazinonic indanone type (called below "compounds of group IV"), R is an aliphatic chain comprising 2 or 3 carbon atoms, possibly branched by an $R_4$ group (preferably alkyl) comprising from 1 to 4 carbon atoms, and forming a ring-closing bond of this chain with the carbon atom at the 6 position on the benzene ring of the benzoxazinone group.

The general structure of the "benzoxazinonic indanones" is then as follows:

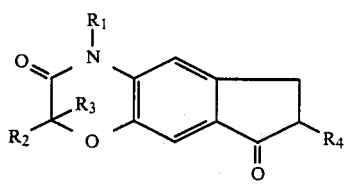

The compounds according to the invention are accessible from the 5-acyl 2-amino phenols described in patent F2 73.23282 filed by the National Institute of Health and Medical Research or again in Eur. J. Med. Chem. 1974, 9, 491, and having the formula:

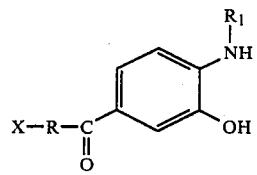

in which $R_1$ has the above-indicated meaning, R and X have the meanings corresponding to those which have been indicated above.

The 5-acyl 2-amino phenols, in which $R_1$ is hydrogen have been obtained by hydrolysis of corresponding 6-acyl benzoxazolinones and under the conditions described in the patent. To produce the 5-acyl 2-amino phenols in which $R_1$ is, for example, a methyl group, the following operational method is employed:

heat the corresponding 6-acyl 3-methyl bensoxazolinonic derivatives in an aqueous solution of 20% caustic soda for one hour at 80° C. (until it has dissolved in the medium). Filter and acidify hot with a concentrated hydrochloric acid solution, then make alkaline with a sodium carbonate solution to pH 8; drain the precipitate, and wash with water until neutrality of the filtrate and recrystallizein a suitable solvent.

A preferred process of the invention to obtain the "compound of group I" comprises a condensation reaction between a derivative of the corresponding aminophenol of the formula:

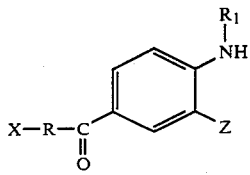

in which $R_1$, R and X have the above-indicated meanings and Z is hydrogen (the reaction being then preferably conducted in an alkaline medium) an alkali metal, particularly sodium, and an alphahalogenic ester of the formula:

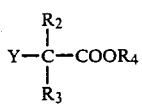

in which $R_2$ and $R_3$ have the above-indicated meanings, Y is halogen, particularly bromine, and $R_4$ an alkyl group, particularly methyl or ethyl, or alkaryl, aralkyl or aryl.

It will be noted that this process is also directly applicable to the manufacture of the compounds of other groups.

A preferred process for obtaining the compounds of group II is obtained by subjecting the compounds of group I in which R—X form an alkyl or arylalkyl group, for example n-propyl, to a reaction in the presence of formaldehyde and amine in an acetic acid medium or in the presence of a reagent such as N'N'N'N'-tetramethyl diamino-methane in the same medium.

To form the "chalcones" or "compounds of the third group", a preferred process consists, starting from a "compound of the first group", of treating it in an organic solvent with the aldehyde X—W—CHO, in which X and W have the above-indicated meanings, in particular benzoic aldehyde.

To form the compounds of the above-indicated prefered fourth class, that of the benzoxazinonic indanones, ring formation of the corresponding alpha, beta ethylenic (or propylenic) ketone is carried out in a concentrated acid medium (particularly in a concentrated sulfuric acid solution).

It will be seen immediately by the technician skilled in the art that other modifications of this manufacturing process (or passage from a compound according to the invention to another compound according to the invention) may be envisaged, without these modifications ceasing to constitute equivalence of the prefered variants which have been defined in the foregoing description.

In a fifth preferred class of compounds according to the invention R is an aliphatic hydrocarbon group containing at least 3 carbon atoms preferably at least 4.

Additional characteristics of the invention will appear also in the course of description which follows of methods of employing the different variants of the process according to the invention which have been described, and of the characteristics both chemical and biological of the products obtained by way of example.

7-ACYL BENZOXAZINONES

General Structure

EXAMPLE 1: Preparation of the "compounds of group 1"

The general operational method as follows was used:
The raw materials of these derivatives are 2-amino 5-acyl phenols.

In a 100 cm$^3$, flask, dissolve 0.03 mole of aminophenol in 60 cm$^3$ of DMSO. Apply magnetic stirring, add 0.03 mole of sodium ethylate so as to form the phenate. Add drop by drop 0.03 mole of an α halogenic ester

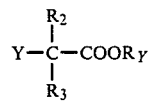

in which Y, $R_2$, $R_3$, and $R_4$ have the above-indicated meanings. Apply a calcium chloride guard and continue the stirring for three hours at ambient temperature. Pour the reaction mixture into 500 cm$^3$ of ice water. Drain the precipitate formed, wash with water until the filtrate is neutral. Dry and recrystallize the precipitate in a suitable solvent. The employment of this process has enabled the following products to be obtained:

1/ 7-Benzoyl benzoxazinone (MZ 114)

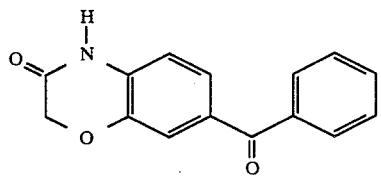

M.W.=253.25 for $C_{15}H_{11}NO_3$
m.p.=208°–210° C.
Recrystallization solvent: acetone
Yield: 75–80%

2/ 7-Benzoyl 2-methyl benzoxazinone (MZ 115)

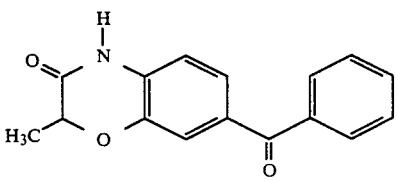

M.W.=267.27 for $C_{16}H_{13}NO_3$
m.p.=158°–160° C.
Recrystallization solvent: 95° alcohol
Yield: 75–80%

3/ 7-Benzoyl 2,2-dimethyl benzoxazinone (MZ 116)

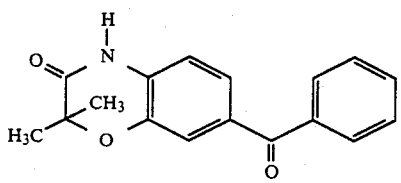

M.W.=281.29 for $C_{17}H_{15}NO_3$
m.p.=212° C.
Recrystallization solvent: acetone or acetonitrile
Yield: 70%
4/ 7-Benzoyl 4-methyl benzoxazinone (MZ 117)

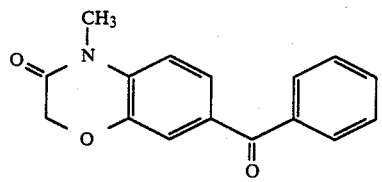

M.W.=267.27 for $C_{16}H_{13}NO_3$
m.p.=118° C.
Recrystallization solvent: methanol
Yield: 80%
5/ 7-Benzoyl 2,4-dimethyl benzoxazinone (MZ 118)

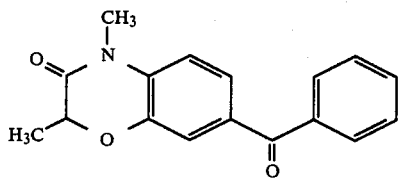

M.W.=281.30 for $C_{17}H_{15}NO_3$
m.p.=128° C.
Recrystallization solvent: methanol
Yield: 75%
6/ 7-Benzoyl 2,2,4 trimethyl benzoxazinone (MZ 119)

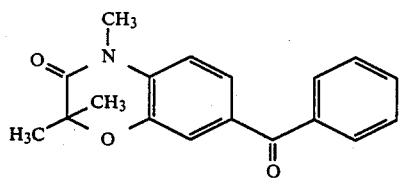

M.W.=295.32 for $C_{18}H_{17}NO_3$
m.p.=122°-124° C.
Recrystallization solvent: methanol
Yield: 75%
7/ 7-(4-Chloro benzoyl)benzoxazinone (MZ 120)

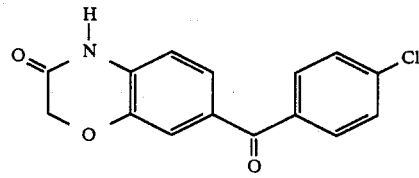

M.W.=287.74 for $C_{15}H_{10}NO_3Cl$
m.p.=242° C.
Recrystallization solvent: 95° alcohol or ethyl acetate
Yield: 50%
8/ 7-(4-Chloro benzoyl)2-methyl benzoxazinone (MX 121)

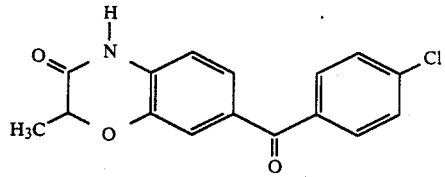

M.W.=301.76 for $C_{16}H_{12}NO_3Cl$
m.p.=185° C.
Recrystallization solvent: acetone or absolute alcohol or 95° alcohol
Yield: 60-65%
9/ 7-(4-Chloro benzoyl)2,2, dimethyl benzoxazinone (MZ 122)

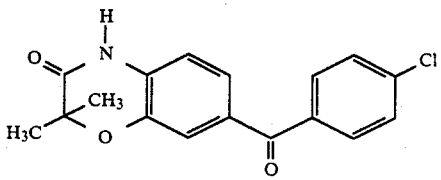

M.W.=315.79 for $C_{17}H_{14}NO_3Cl$
m.p.=185°-187° C.
Recrystallization solvent: 95° alcohol
Yield: 60-65%
10/ 7-(4-Chloro benzoyl)4-methyl benzoxazinone (MZ 123)

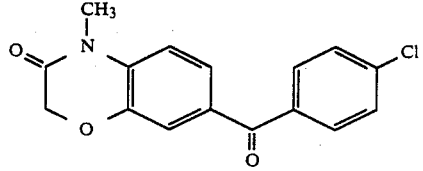

M.W.=301.76 for $C_{16}H_{12}NO_3Cl$
m.p.=190°-192° C.
Recrystallization solvent: benzene
Yield: 70%
11/ 7-(4-Chloro benzoyl)2,4-dimethyl benzoxazinone (MZ 124)

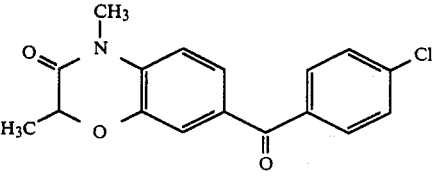

M.W.=315.79 for $C_{17}H_{14}NO_3Cl$
m.p.=113°-115° C.
Recrystallization solvent: absolute alcohol
Yield: 70%
12/ 7-(4-Chloro benzoyl)2,2,4-trimethyl benzoxazinone (MZ 125)

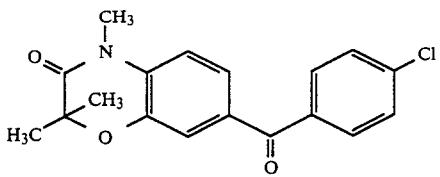

M.W.=329.81 for $C_{18}H_{16}NO_3Cl$
m.p.=130°–132° C.
Recrystallization solvent: absolute alcohol or 95° alcohol
Yield: 60%

13/ 7-Acetyl 2,4-dimethyl benzoxazinone (MZ 132)

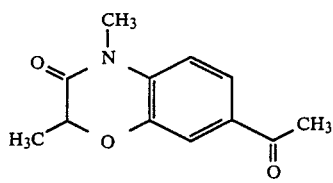

M.W.=219.23 for $C_{12}H_{13}NO_3$
m.p.=132°–134° C.
Recrystallization solvent: methanol
Yield: 75%

14/ 7-Acetyl 2,2,4-trimethyl benzoxazinone (MZ 136)

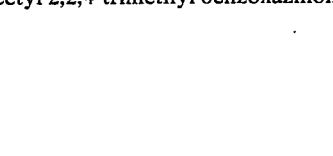

M.W.=223.25 for $C_{13}N_{15}NO_3$
m.p.=100°–102° C.
Recrystallization:
 1-hexane
 2-absolute alcohol
Yield: 75%

15/ 7-Acetyl 4-methyl benzoxazinone (MZ 126)

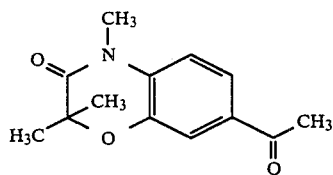

M.W.=205.20 for $C_{11}H_{11}NO_3$
m.p.=150° C.

Recrystallization solvent: absolute alcohol or methanol

Derivatives of 7-acetyl benzoxazinone

Operational method

Dissolve in 60 cm3 of absolute ethanol 1 equivalent of acetyl7 benzoxazinone, 1.3 equivalent of amine chlorhydrate diversely substituted and one equivalent of trioxymethylene. Add to the mixture one drop of concentrated hydrochloric acid. Leave under reflux for the solvent for 40 hours. Add after 1 H 30 and 19 H of reflux 0.5 equivalent of trioxymethylene.

Cool, drain and wash the precipitate with acetone-recrystallize.

16/ 7[3-morpholino propionyl[2'2'4 trimethyl benzoxazinone, hydrochloride (NM7)

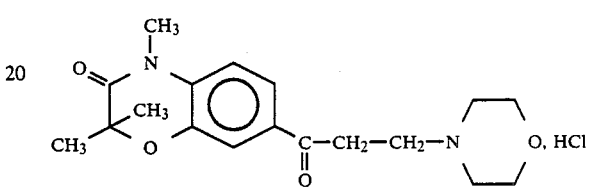

M.W.=363.83 for $C_{18}H_{25}ClN_2O_4$
m.p.=202°–404° C.
Recrystallization solvent: absolute ethanol
Yield: 48%

17/ 3(4-Metatrifluoromethylphenyl piperazino)7-propionyl 2,2,4 trimethyl benzoxazinone, hydrochloride (NM 8)

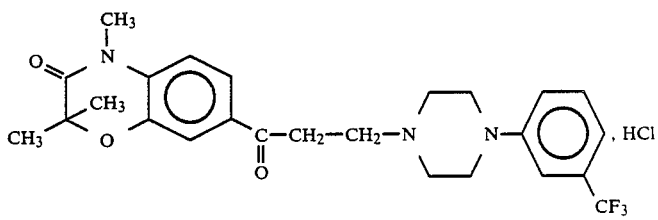

M.W.=511.97 for $C_{25}H_{29}ClF_3N_3O_3$
m.p.=198° C.
Recrystallization solvent: absolute ethanol
Yield: 55%

18/ 7-Butyryl 2,2-dimethyl benzoxazinone (MZ 95)

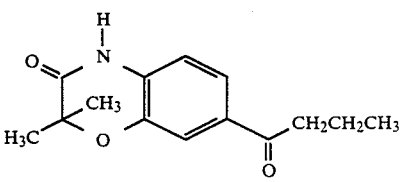

M.W.=247.28 for $C_{14}H_{17}NO_3$
m.p.=137°–139° C.
Recrystallization solvent: methanol
Yield: 70%

19/ 7-Butyryl 4-methyl benzoxazinone (MZ 81)

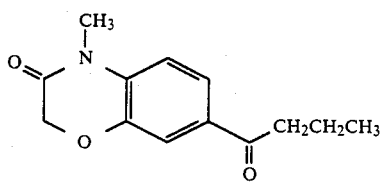

M.W. = 233.26 for $C_{13}H_{15}NO_3$
m.p. = 104°–105° C.
Recrystallization solvent: cyclohexane or absolute alcohol
Yield: 85%

20/ 7-Butyryl 2,4-dimethyl benzoxazinone (MZ 85)

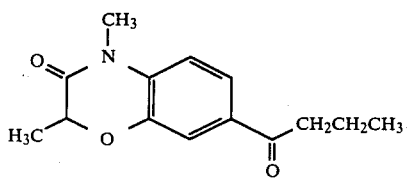

M.W. = 247.28 for $C_{14}H_{17}NO_3$
m.p. = 84° C.
Recrystallization solvent: hexane or cyclohexane
Yield: 75%

21/ 7-Butyryl 2,2,4-trimethyl benzoxazinone (MZ 86)

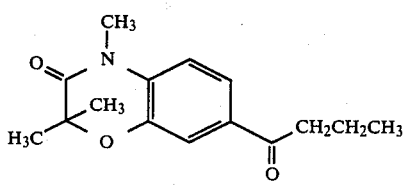

M.W. = 261.30 for $C_{15}H_{19}NO_3$
m.p. = 80° C.
Recrystallization solvent: hexane or absolute alcohol
Yield: 75%

22/ 7-Lauryl 2,4-dimethyl benzoxazinone (NM 4)

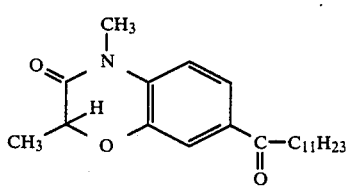

M.W. = 359.48 for $C_{22}H_{33}NO_3$
m.p. = 68°–69° C.
Recrystallization solvent: 95° alcohol
Yield: 55%

23/ 7-Lauryl 2,2,4-trimethyl benzoxazinone (NM 3)

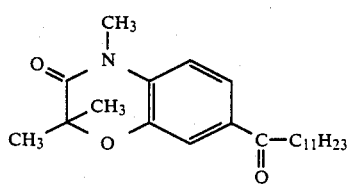

M.W. = 373.50 for $C_{23}H_{35}NO_3$
m.p. = 57°–58° C.
Recrystallization solvent: methanol
Yield: 55%

24/ 7-Valeroyl 2,4-dimethyl benzoxazinone (NM 17)

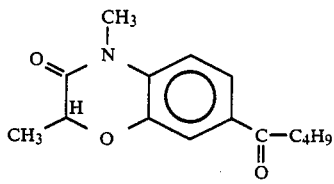

M.W. = 261.30 for $C_{15}H_{19}NO_3$
m.p. = 76° C.
Recrystallization solvent: hexane
Yield: 70%

25/ 7-Butyryl 4-β cyanoethyl 2,2 dimethyl benzoxazinone (NM 14)

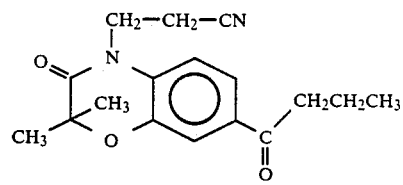

Operational method:
In a ground glass Erlenmeyer flask, dissolve with stirring 0.01 mole of butyryl 2,2-dimethyl benzoxazinone (MZ 95) in 100 cm3 of ether. Add drop by drop 0.02 mole of acrylonitrile with vigorous stirring then 0.4 cm3 of Triton B. Leave for 36 hours under reflux, with stirring. Filter the ether solution and evaporate off the excess ether. Drain the precipitate obtained, rinse it with ether, dry and recrystallize.

M.W. = 300.36 for $C_{17}H_{20}N_2O_3$
m.p. = 90°–91° C.
Recrystallization solvent: Hexane
Yield: 86%

26/ 7-Butyryl 4-β carboxyethyl 2,2-dimethyl benzoxazinone (NM 11)

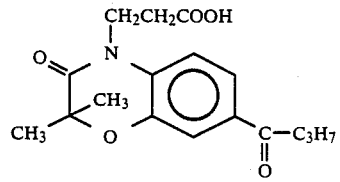

Operational method:
Bring to reflux for 105 minutes, a reaction mixture composed of 0.02 mole of NM 14, 10 cm³ of acetic acid, 10 cm³ of concentrated sulfuric acid and 10 cm³ of water.

After cooling, add 20 cm³ of water. Drain and wash the precipitate formed with water. Dry and recrystallize.

M.W. = 311.36 for $C_{17}H_{21}NO_5$
m.p. = 146° C.
Recrystallization solution: 50° ethanol
Yield: 77%

27/ 7-(4-hydroxy butyryl)4-methyl benzoxazinone (MZ 48)

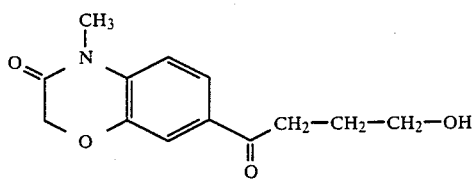

M.W.=249.25 for $C_{13}H_{15}NO_4$
m.p.=130° C.
Recrystallization solvent: absolute alcohol
Yield: 75%

28/ 7(4-hydroxy butyryl)2,2,4-trimethyl benzoxazinone (MZ 150)

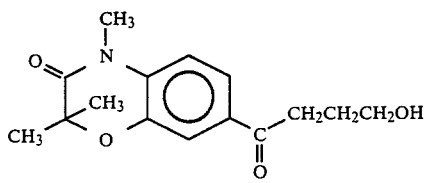

M.W.=277.31 for $C_{15}H_{19}NO_4$
m.p.=83° C.
Recrystallization solvent: water
Yield: 60%

29/ 7-(4-bromo butyryl)4-methyl benzoxazinone (MZ 49)

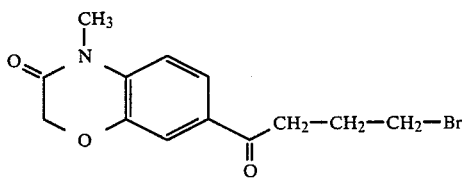

M.W.=312.25 for $C_{13}H_{14}NO_3Br$
m.p.=122°-124° C.
Recrystallization solvent: absolute alcohol
Yield: 80%

It is prepared by the action of gazeous hydrobromic acid on the compound MZ 48 by operating as follows: Dissolve the compound MZ 48 in anhydrous benzene. Whilst ensuring moderate magnetic stirring, bubble hydrobromic acid into the solution watching the weight take up and leave the reaction medium in an oil bath at 40° C. and with stirring for two hours. Filter and evaporate the solvent under vacuum and recrystallize in absolute alcohol.

30/ 7(4-bromo butyryl)2,2,4-trimethyl benzoxazinone (MZ 151)

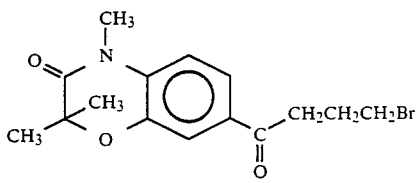

M.W.=340.30 for $C_{15}H_{18}NO_3Br$
m.p.=111° C.
Recrystallization solvent: absolute alcohol
Yield: 80%

31/ 7-[4-(dimethylamino)]butyryl 4-methyl benzoxazinone (MZ 50)

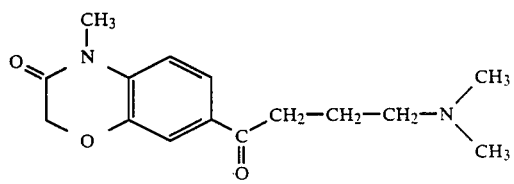

It is possible to proceed by condensation of amines: Dissolve with heating 7-(4-bromo butyryl)4-methylbenzoxazinone in anhydrous benzene. Add with stirring the corresponding amine, then an equivalent amount of triethylamine. Heat under reflux for fifteen hours, then drain the precipitate formed hot (triethylamine salt).
Evaporate the filtrate under vacuum and recrystallize the residue.
M.W.=276.32 for $C_{15}H_{20}N_2O_3$
m.p.=98°-100° C.
Recrystallization solvent: Hexane
Yield: 50%

32/ [4(dimethylamino)butyryl]2,2,4-trimethyl benzoxazinone (MZ 154)

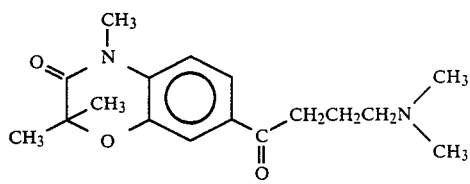

M.W.=304.38 for $C_{17}H_{24}N_2O_3$
m.p.=67° C.
Recrystallization solvent: hexane
Yield: 50%

33/ 7-[4(4-phenyl piperazino)butyryl]2,2,4-trimethyl benzoxazinone (MZ 152)

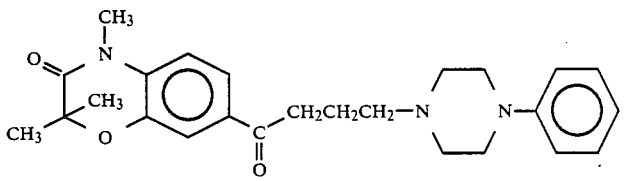

M.W.=421.52 for $C_{25}H_{31}N_3O_3$
m.p.=131° C.
Recrystallization solvent: absolute alcohol
Yield: 65%

34/ 7[4(4p-fluorophenyl piperazino)butyryl]2,2,4-trimethyl benzoxazinone (MZ 153)

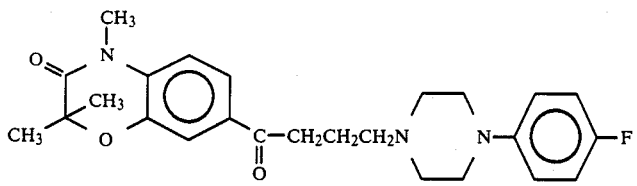

M.W.=439.51 for $C_{25}H_{30}FN_3O_3$
m.p.=82°–84° C.
Recrystallization solvent: isopropanol
Yield: 60%

35/ 7-[4(4m-Methoxyphenyl piperazino)-butyryl]2,2,4-trimethyl benzoxazinone (MZ 155)

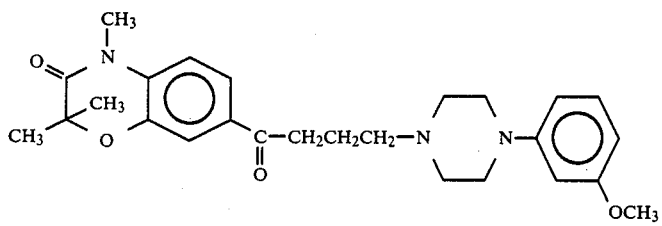

M.W.=451.55 for $C_{26}H_{33}N_3O_4$
m.p.=118° C.
Recrystallization solvent: methanol
Yield: 55%

36/ 7-Cyclopropoyl 4-methyl benzoxazinone (MZ 82)

First is prepared the 5-acyl 2-amino phenol MZ 83 of the formula:

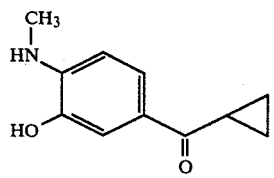

from 6-(4-bromo butyryl)3-methyl benzoxazolinone by treating it in a strong basic medium, more particularly with a 20% sodium hydroxide solution. It is heated for one hour at 80° C. then this solution is cooled and it is neutralized with a dilute hydrochloric acid solution (pH 6.5–7). In this manner opening of the benzoxazolinonic ring and dehalohydrogenation at the alpha position of its ketone group have been effected therefore simultaneously. The chemical characteristics of the product MZ 83 are as follows:

M.W.=191.22 for $C_{12}H_{13}NO_2$
m.p.=170°0 C.
Recrystallization solvent: half-diluted alcohol From the product MZ 83 the product MZ 82 of the formula:

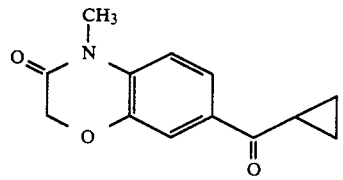

is then formed by employing the operational procedure of example I.

M.W.=231.24 for $C_{13}H_{13}NO_3$
m.p.=110°–112° C.
Recrystallization solvent: cyclohexane or 95° alcohol
Yield: 80%

37/ 7-cyclopropoyl2,4 dimethyl benzoxazinone (MZ 87)

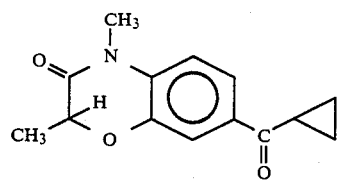

M.W.=245.52 for $C_{14}H_{15}NO_2$
m.p.=87° C.
Recrystallization solvent: cyclohexane
Yield: 80%

38/ 7-cyclopropoyl2,2,4 trimethyl benzoxazinone (MZ 88)

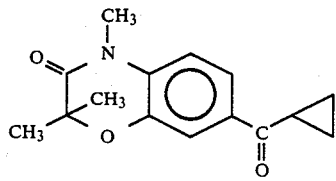

M.W.=259.29 for $C_{15}H_{17}NO_2$
m.p.=51°–53° C.
Recrystallization solvent: hexane
Yield: 50%

39/ 7-Thenoyl 4-methyl benzoxazinone (MZ 145)

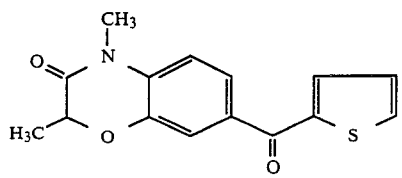

It is prepared under similar conditions to those which have been envisaged in the preceding examples.
M.W.=287.32 for $C_{15}H_{13}NO_3S$
m.p.=120°-124° C.
Recrystallization solvent: absolute alcohol or isopropanol or propanol
Yield: 75%

EXAMPLE II: Preparation of "compounds of group II"

The operational method applied to the following raw materials, is of general application:
7-butyryl 4-methyl benzoxazinone
N'N'N'N'-tetramethyl diamino methane
acetic anhydride.

In a ground glass flask of 100 cm3, place in suspension 0.02 moles of the derivative of 7-butyryl 4-methyl benzoxazinone in 10 cm³ of N'N'N'N'-tetramethyl-diaminomethane. Add drop by drop and with magnetic stirring 10 cm³ of acetic anhydride, and heat the reaction medium to 90° C. for two hours. Cool to ambient temperature and pour the reaction mixture into 300 cm³ of ice water. Drain the precipitate and wash with water until neutrality of the filtrate. Dry and recrystallize is a suitable solvent.

1/ 7-(2-Methylene butyryl)4-methyl benzoxazinone (MZ 78)

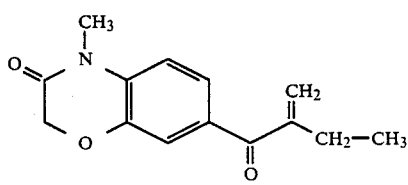

M.W.=245.27 for $C_{14}H_{15}NO_3$
m.p.=76°-78° C.
Recrystallization solvent: methanol
Yield: 80%
2/ 7-(2-Methylene butyryl)2,4-dimethyl benzoxazinone (Mz 79)

M.W.=259.29 for $C_{15}H_{17}NO_3$
m.p.=51°-52° C.
Recrystallization solvent: ether
Yield: 80%
3/ 7-(2-Methylene butyryl)2,2,4-trimethyl benzoxazinone (MZ 77)

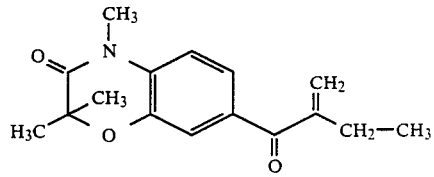

M.W.=273.32 for $C_{16}H_{19}NO_3$
m.p.=66°-68° C.
Recrystallization solvent: hexane or absolute alcohol
Yield: 80%
4/ 7-[4(4-phenyl piperazino)2-methylene butyryl]2,2,4-trimethyl benzoxazinone (MZ 158)

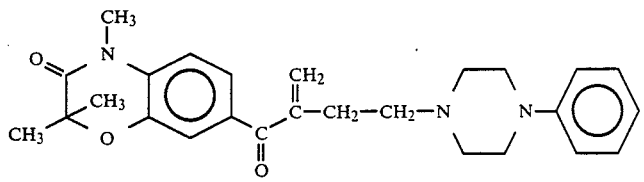

M.W.=433.55 for $C_{26}H_{31}N_3O_3$
m.p.=82°-84° C.
Recrystallization solvent: absolute ethanol
Yield: 50%
5/ 7-[2-Methylene 3-acetoxy propionyl]2,2,4-trimethyl benzoxazinone (MZ 147)

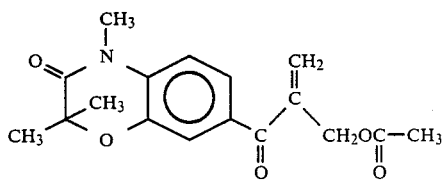

M.W.=317.33 for $C_{17}H_{19}NO_5$
m.p.=110° C.
Recrystallization solvent: methanol
Yield: 55%

EXAMPLE III: Preparation of "compounds of group III"

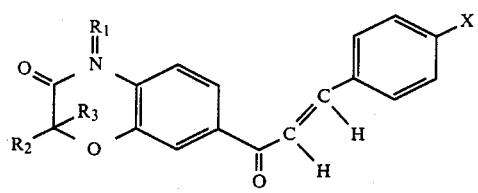

Operational method used:
Dissolve 0.03 moles of 7-acyl benzoxazinone in 150 cm³ of absolute ethanol saturated with gazeous hydrochloric acid, then add slowly, and with magnetic stirring, 0.035 mole of the corresponding aldehyde.

Continue with the stirring for two hours. The expected product preciptitates in the reaction medium. Drain and wash the precipitate with absolute alcohol, then with water until neutrality of the filtrate. Dry and recrystallize in a suitably selected solvent 1/ 7-(4-Chloro cinnamoyl)4-methyl benzoxazinone (MZ 129)

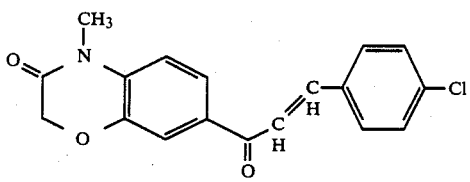

M.W. = 327.81 for $C_{18}H_{14}ClNO_3$
m.p. = 209°
Recrystallization solvent: acetone
Yield: 70%

2/ 7(4-Chloro cinnamoyl)2,4 dimethyl benzoxazinone (MZ 134)

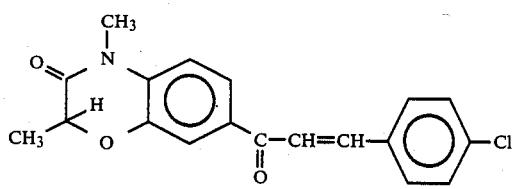

M.W. = 341.82 for $C_{19}H_{16}ClNO_3$
m.p. = 125° C.
Recrystallization solvent: absolute alcohol
Yield: 70%

3/ 7(4-Chloro cinnamoyl)2,2,4 trimethyl benzoxazinone (MZ 137)

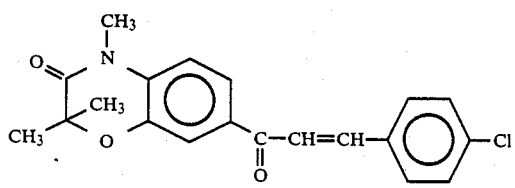

M.W. = 335.85 for $C_{20}H_{18}ClNO_3$
m.p. = 166°–167° C.
Recrystallization solvent: absolute ethanol
Yield: 65%

4/ 7-(4-hydroxy cinnamoyl)4-methyl benzoxazinone (MZ 130)

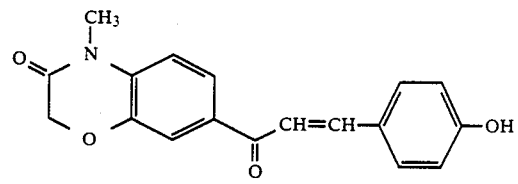

M.W. = 309.30 for $C_{18}H_{15}NO_4$
m.p. = 222°–225° C.
Recrystallization solvent: acetone
Yield: 70%

5/ 7(4-hydroxy cinnamoyl)2,4 dimethyl benzoxazinone (MZ 133)

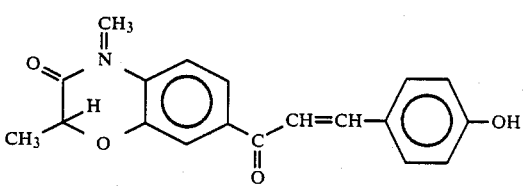

M.W. = 323.33 for $C_{19}H_{17}NO_4$
m.p. = 226° C.
Recrystallization solvent: acetone
Yield: 75%

6/ 7(4-hydroxy cinnamoyl)2,2,4 trimethyl benzoxazinone (MZ 139)

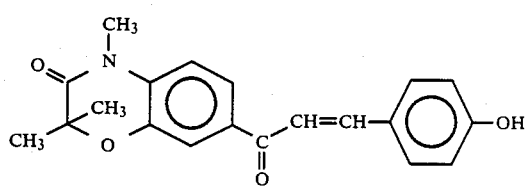

M.W. = 337.36 for $C_{20}H_{19}NO_4$
m.p. = 228° C.
Recrystallizationn solvent: acetone
Yield: 60%

7/ 7-Cinnamoyl 4-methyl benzoxazinone (MZ 131)

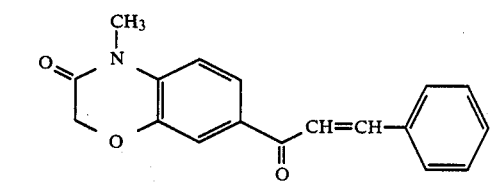

M.W. = 293.30 for $C_{18}H_{15}NO_3$
m.p. = 134°–136° C.
Recrystallization solvent: absolute alcohol
Yield: 70%

8/ 7-Cinnamoyl 2,4 dimethyl benzoxazinone (MZ 135)

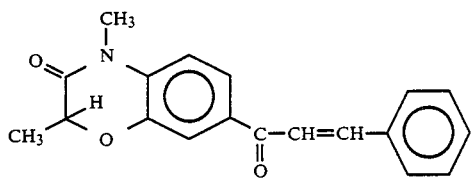

M.W.=307.33 for $C_{19}H_{17}NO_3$
m.p.=135° C.
Recrystallization solvent: absolute ethanol
Yield: 70%

9/ 7-Cinnamoyl 2,2,4 trimethyl benzoxazinone (MZ 138)

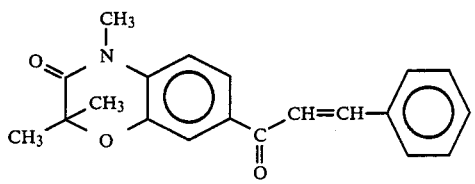

M.W.=321.36 for $C_{20}H_{19}NO_3$
m.p.=136°-138° C.
Recrystallization solvent: absolute ethanol
Yield: 65%

EXAMPLE IV: Preparation of the compound of group IV

Operational method used:
Derivatives of alpha-beta ethylene ketones ("compounds of group II") are used as raw materials. Dissolve 0.03 mole of the alpha-beta ethylenic ketone in 30 ml of concentrated sulfuric acid (98%) then leave the reaction medium with stirring at room temperature (18°-25° C.) for fifteen hours. Pour this medium into 300 ml of ice water. Drain the precipitate formed in this medium, wash several times with cold water until neutrality of the filtrate. Dry and recrystallize in a suitable solvent.

1/ 4H-2,3-dihydro 3,8-dioxo 4-methyl cyclopenta (g)benzoxazine (MZ 84)

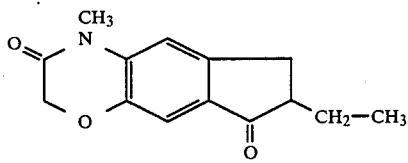

M.W.=245.27
m.p.=147° C.
Recrystallization solvent: acetone
Yield: 90%

2/ 4H 2,3-dihydro 3,8-dioxo 2,2,4-trimethyl 7-methylene cyclopenta (g) benzoxazine (MZ 148)

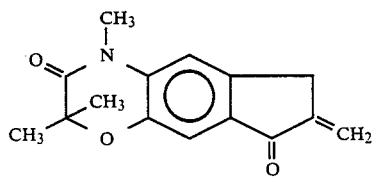

M.W.=257.27 for $C_{15}H_{15}NO_3$
m.p.=184° C.
Recrystallization solvent: acetone
Yield: 65%

3/ 4H 2,3-dihydro 3,8-dioxo 2,4-dimethyl 7-ethyl cyclopenta (g) benzoxazine (MZ 89)

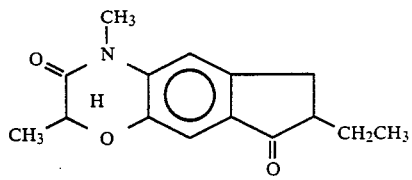

M.W.=259.29 for $C_{15}H_{17}NO_3$
m.p.=120°-122° C.
Recrystallization solvent: methanol
Yield: 75%

4/ 4H 2,3-dihydro 3,8-dioxo 2,2,4-trimethyl 7-ethyl cyclopenta (g) benzoxazine (MZ 90)

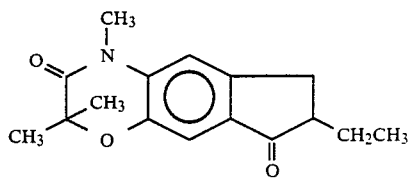

M.W.=273.32 for $C_{16}H_{19}NO_3$
m.p.=110°-112° C.
Recrystallization solvent: methanol
Yield: 80%

RESULTS RELATING TO THE BIOLOGICAL PROPERTIES OF THE COMPOUNDS ACCORDING TO THE INVENTION

The pharmacological study of the compounds of the invention has shown that they possess interesting properties.

1/ TOXICITY

The toxicity of the compounds has been determined by the oral route, in the rat.
All the compounds have an $LD_{50}$ higher than 2000 mg/kg.

2/ ANTIATHEROSCLEROSIS ACTIVITY

Considerable efforts have been expended for some time to find substances which can counter the consequences of hyperlipemia: hypercholesterolemia, unbalance of the apoprotein ratio $A_1$/B or of the LDL Cholesterol/HDL Cholesterol ratio (with LDL: low density lipoproteins and HDL: high density lipoproteins) these lipoproteins being separated by density gradients. The most important repercussion of hyperlipemia is atherosclerosis. This is the most frequent cause of coronary disease, of arteriopathies, and of cerebral vascular disorders.

The study of FRAMINGHAM (Castelli W. P. et col., Circulation 1977, 55, 767.772) has enabled a correlation to be established between high total cholesterol levels and an increase in the risk of cardiac attack as well as the correlation between high HDL cholesterol levels and the diminution of the same risk.

The prevention, the arrest or the treatment of atherosclerosis necessitates treating the hyperlipemia.

Numerous hypolipemic agents are now available: clofibrate, cholestyramine, gemfibrozil, probucol . . . .

The development of novel products devoid of side effects, which can reduce the total cholesterol, the triglycerides, re-establish the balances ApoA$_1$/Apo B, HDL cholesterol/LDL cholesterol and TXA$_2$/PGI$_2$, TXA$_2$ being thromboxane A$_2$ and PGI$_2$ being prostacycline, is sought by the medical community for the treatment and prevention of atherosclerosis. Oral forms are necessary since the patients are called to take these medicaments for many years.

The products of this invention are original and possess interesting pharmacological properties.

They have an original chemical structure and have an activity superior to other hypolipemic agents at present on the market. These novel compounds are well absorbed by the gastro intestinal tract and are devoid of side effects particularly an absence of hepatomegalia and proliferation of peroxysomes.

These products have been tested to confirm their activity with respect to atheromatous disturbances.

The various points below have been studied:
Test with Triton, surface active detergent marketed under the name WR 1339, in the rat.
Activity of selected molecules by the Triton test in mice rendered hypercholesterolemic and normal mice: study of the lipid parameters, of the lipoprotein and apoprotein composition.
Preliminary study on the weight of the liver and histological examination of the hepatic tissue.
Platelet antiagregating activity according to conventional tests (in vitro, on human blood).

3/ NORMOLIPEMIC ACTIVITY:

3.1 The normolipemic activity of the compounds was established by the conventional method of the test employing the detergent as in the commercial name Triton. This method is described in the following articles: Kellner A. and Coll. J. of Experimental Med. 1951, vol 93, p. 373-385 and in Schurr P. E. and Coll. Lipids 1952, vol 7, no. 1, 68-74. The results are summarized in the following table.

All the compound were administered orally to the rat, at the rate of 300 mg/kg. By way of comparison, the results obtained with fenofibrate at the same dose are provided.

The results obtained are to the advantage of the compounds according to the invention, especially if account is taken of the total absence of toxicity which characterizes them. There can also be noted the better activity of the derivatives substituted at the 7 position with respect to their homolog substituted at the 6 position as well as that of acylic derivatives on the aromatic nucleus with respect to their reduced homologs.

| | VARIATION OF THE % ACTIVITY WITH RESPECT TO THE TRITON CONTROL | | | |
|---|---|---|---|---|
| | Total Cholesterol | HDL Cholesterol | Triglycerides | Apo B |
| MZ 77 | 50,1 | 29 | 85 | 15,3 |
| MZ 78 | 54,6 | 72,4 | 89,7 | 34,2 |
| MZ 79 | 56,9 | 72,4 | 89,3 | 35 |
| MZ 86 | 46,3 | 69,3 | 67,5 | 43.8 |
| * | 28,0 | 30,0 | 15,0 | ND |
| MZ 95 | 33,0 | 15,6 | 48,0 | 26.8 |
| MZ 114 | 52,5 | 25,9 | 74,2 | ND |
| MZ 115 | 48,2 | 46,6 | 78,3 | ND |
| MZ 116 | 43,1 | 20,4 | 68,9 | ND |
| MZ 117 | 45,1 | 43,9 | 72,0 | ND |
| MZ 118 | 54,6 | 18,8 | 77,3 | ND |
| reduced MZ118 | 15,0 | 29,0 | 25,0 | ND |
| MZ 119 | 50,1 | 43,3 | 73,9 | ND |
| MZ 120 | 19,2 | ND | 19,7 | 14.3 |
| MZ 121 | 26,5 | 7,9 | 45,3 | 26,2 |
| MZ 122 | 24,2 | 0 | 37,3 | 23.8 |
| MZ 123 | 34,8 | 16,7 | 50,1 | 27.9 |
| MZ 124 | 36,5 | 19,2 | 61,1 | 29,2 |
| MZ 125 | 26,8 | 10,3 | 47,0 | 26,7 |
| MZ 126 | 19,5 | 13,2 | 20,5 | 21 |
| MZ 129 | 63,3 | 29,8 | 81,8 | 32 |
| MZ 130 | 55,7 | 44,8 | 75,5 | 35 |
| MZ 131 | 62,9 | 23 | 82,6 | 32 |
| MZ 132 | 22,2 | 21,5 | 5,8 | 17 |
| MZ 136 | 31,0 | 42,0 | 29,5 | ND |
| Fenofibrate | 36,5 | 48,3 | 64,5 | 19,5 |

*Homologue of MZ 86 substituted at the 6 position.

3.2 The normolipemic activity has also been established in OF normal mice or rendered hypercholesterolemic. The products tested were administered per os daily for 15 days at the dose of 50 mg/kg. The change in weight was observed in the course of the treatment, a lipid balance was effected at the end of the experimentation with respect to a control group.

The results are summarized in the following table. All the compounds were administered orally at the rate of 50 mg/kg.

It is known that HDLs constitute the "purifying fraction" of cholesterol. HDLs transport the cholesterol to convert it at the level of the liver into biliary salts which are eliminated by the bile.

| CONTROL | Liver weight Body weight | CT (1) % | HDL$_C$/TC (2) % | TG (3) % | HDL$_C$ (4) % | Phospho Lipids |
|---|---|---|---|---|---|---|
| FENOFIBRATE | +55% | −30% | +30% | +24% | −11% | +18% |
| MZ 86 | +2% | −38% | +44% | −12% | +18% | 0% |
| MZ 95 | +6% | −21% | +25% | −5% | 0 | +5% |
| MZ 115 | +9% | −32% | +17% | +18% | −5% | −9% |
| MZ 119 | +12% | −30% | +21% | +21% | −6% | +15% |
| MZ 125 | +17% | −25% | +18% | +19% | +1% | +15% |
| MZ 134 | +5% | 31 5% | +10% | −9% | +5% | +11% |
| MZ 153 | +4% | −10% | +45% | +18% | +25% | +19% |
| NM 7 | −10% | +2% | +14% | +5% | +5% | +5% |
| NM 8 | −15% | +8% | +11% | +23% | +10% | +8% |
| NM 11 | 0% | −37% | +43% | −8% | +7% | +16% |

(1) CT = Total cholesterol
(2) HDL (c)/CT = ratio between the cholesterol contained in the HDLs and the total cholesterol
(3) Triglycerids
(4) Cholesterol fraction contained in the HDLs 3.3 Inhibiting activity of platelet agregation.

The inhibiting effect of various B aminoketones on platelet agregation has already been described. (CAZIN and col. Acta Therapeutic 1980, 6, 205-211). Pharmacological studies carried out on certain molecules of the present invention have confirmed that this inhibiting activity is manifested by an antithrombotic and platelet anti-aggregating activity. This activity is very interesting especially if it is associated with a hypolipemic activity; it permits a new approach of anti-atherosclerosis therapy.

Inhibition of the in vitro platelet aggregation was tested by the procedure described by ASHIDA and col. Thrombosis Haemostasis 1979, 40, 542.

| INHIBITING ACTIVITY OF PLATELET AGGREGATION INDUCED BY SODIUM ARACHIDONATE AND COLLAGEN | | |
|---|---|---|
| Product Reference | Arachidonate $DE_{50}$ (mg/kg) | Collagene $DE_{50}$ (mg/kg) |
| Aspirine | 37 | 59,5 |
| NM 7 | 1,92 | 2,72 |
| NM 8 | 11,61 | 15,00 |
| MZ 130 | 0,15 | 0,19 |
| MZ 154 | 0,26 | 0,92 |
| MZ 133 | 6,10 | 11,00 |
| MZ 85 | 21,00 | 22,00 |

4/ Other pharmacological activities

In preliminary pharmacological tests, a certain number of other activities were demonstrated in certain products particularly analgesic, sedative, anti-inflammatory, antimicrobial, antifungal, cardiovascular properties particularly on dopaminergic receptors, and on the central nervous system.

The invention relates more particularly to pharmaceutical compositions employing the compounds according to the invention in association with a pharmaceutically acceptable vehicle. Preferably, the compositions according to the invention are in an administrable form, preferably oral, and particularly in solid form.

They may be offered in any forms suitable for this method of administration, for example in pills, tablets, etc.

EXAMPLE OF GALENIC FORMULATION

| 7-Butyryl 2,2,4-trimethyl benzoxazinone | 100 mg |
|---|---|
| Magnesium stearate | 1 mg |
| Talc | 5 mg |
| Corn starch | 20 mg |
| Weight of the contents of the capsule | 126 mg |

The compounds according to the invention are useful for the treatment of atheromatous disorders involving particularly lipids or glycerides.

Besides, the compositions according to the invention are characterised by an analgesic, anti-inflammatory, sedative, antibacterial, antifungal, cardiovascular activity and an activity on the central nervous system.

The total absence of toxicity confers them a particularly favorable therapeutical index.

The compositions are advantageously prepared in order to allow the administration of unit doses of 1 to 500 mg, when considering more particularly the oral route. Ranges of daily doses useful for the adult can be etablisched between 5 and 1000 mg by day.

It is obvious that other derivatives having the principal basic structures or the preferred one, which are considered in the specification, are included into the scope of the invention as claimed. Molecules which would be distinct of those more particularly claimed, only because of the presence of non expressly identified substituents in the claims, but which would not be capable to considerably modify the biological properties of said derivatives, are indeed comprised into the scope of the invention.

The invention relates also to the use of the above mentioned components for manufacturing medicaments intended for treatment of cardio-vascular disorders, involving in particular lipids or glucids, or intended for use as analgesic, anti-inflammatory or antifungal components.

We claim:

1. A method for treating atheromatous disorders comprising the step of administering an effective amount of a compound selected from the group consisting of a 7-acyl benzoxazinone compound of the formula:

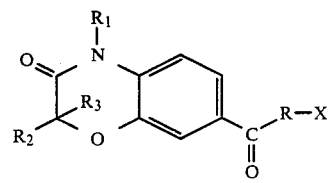

in which:
$R_1$ is hydrogen, a heterocyclic group or a hydrocarbon group of 1 to 6 carbon atoms which may be substituted with a carboxyl, halogen, hydroxy, nitro, alkoxy of 1 to 4 carbon atoms or amino which may be substituted with one or two alkyl groups that are of 1 to 4 carbon atoms;

$R_2$ and $R_3$ are each, independently of one another, hydrogen or alkyl of 1 to 6 carbon atoms;

R is a divalent hydrocarbon group of 1 to 15 carbon atoms or a divalent heterocyclic group; and X is hydrogen, carboxyl, halogen, hydroxy, a heterocyclic group, nitro, alkoxy of 1 to 4 carbon atoms or amino which may be substituted with one or two alkyl groups that are of 1 to 4 carbon atoms or X can form a chemical ring-forming bond between R and the carbon atom at the 6-position of said compound;

and the salts, esters and optical isomers thereof.

2. The method of claim 1, wherein $R_1$ is an alkyl of 1 to 6 carbon atoms.

3. The method of claim 1, wherein $R_1$ is a heterocyclic group selected from the group consisting of thienyl, furyl, pyridinyl and pyridyl.

4. The method of claim 1, wherein $R_1$, $R_2$ and $R_3$ are hydrogen or methyl.

5. The method of claim 1, wherein R is a divalent alkylene of 1 to 6 carbon atoms, arylene, arylenealkylene or alkylenearylene or a divalent heterocyclic group; and X is hydrogen, halogen, hydroxyl, amino or a heterocyclic group.

6. The method of claim 5, wherein R is $-C_6H_4-$, $-CH_2C_6H_4-$ or cyclopropylene.

7. The method of claim 5, wherein R is a divalent heterocyclic group selected from the group consisting of thienylene, furylene, pyridinylene and pyridylene and/or X is a monovalent heterocyclic group selected from the group consisting of thienyl, furyl, pyridinyl and pyridyl.

8. The method of claim 1, wherein R is a divalent aliphatic hydrocarbon chain with a first carbon having an ethylenic branching group.

9. The method of claim 1, wherein X is a heterocyclic amino group.

10. The method of claim 9, wherein X is a piperazine group.

11. The method of claim 1, wherein R is a divalent hydrocarbon of a divalent heterocyclic group of at least 3 carbon atoms.

12. The method of claim 11, wherein R is a divalent hydrocarbon group of at least 4 carbon atoms.

13. The method of claim 12, wherein R is —C≡C—W—X, in which: W is an alkylene, arylenealkylene, alkylenearylene or arylene group.

14. The method of claim 13, wherein R is a 2-methylene-butyryl group.

15. The method of claim 13, wherein —R—X is —C≡C—$C_6H_5$—X and X is hydrogen, halogen, amino, hydroxy, methoxy or nitro.

16. The method of claim 15, wherein X is chlorine or bromine.

17. The method of claim 1, wherein R is a divalent aliphatic hydrocarbon chain of 2 or 3 carbon atoms and X is a branching substituent on R and is an alkyl of 1 to 4 carbon atoms that forms a heterocyclic group with R and the carbon atom at the 6-position of said compound.

* * * * *

UNITED STATES PATENT AND TRADEMARK OFFICE
CERTIFICATE OF CORRECTION

PATENT NO. : 4,778,792

DATED : Oct. 18, 1988

INVENTOR(S) : I. Lesieur, C. Lespagnol, Z. Moussavi, J-C Fruchart, J. Sauzieres, N. Monfilliette It is certified that error appears in the above-identified patent and that said Letters Patent is hereby corrected as shown below:

Col. 1, line 31, after "hydrogen", insert --or a hydrocarbon--;

Col. 1, line 46, "containing" should be --comprising--;

Col. 2, line 9, "-C=-X-X" should be "-C=C-W-X";

Col. 3, line 56, "preferred" is misspelled;

Col. 8, line 26, "363.83" should be --368.83--;

Col. 22, second table from the bottom, third column, where it states "CT (1)%, "31 5%" should be -- -5% --;

Col. 25, line 6, claim 11, "of a divalent" should be --or a divalent--.

Signed and Sealed this

Fourteenth Day of March, 1989

Attest:

DONALD J. QUIGG

Attesting Officer

Commissioner of Patents and Trademarks